(12) United States Patent
Barrett et al.

(10) Patent No.: US 7,019,033 B2
(45) Date of Patent: Mar. 28, 2006

(54) 2-(4-BROMO OR 4-IODO PHENYLAMINO) BENZOIC ACID DERIVATIVES

(75) Inventors: Stephen Douglas Barrett, Livonia, MI (US); Alexander James Bridges, Saline, MI (US); Donna Reynolds Cody, Saline, MI (US); Annette Marian Doherty, Paris (FR); David Thomas Dudley, Ann Arbor, MI (US); Alan Robert Saltiel, Ann Arbor, MI (US); Mel Conrad Schroeder, Dexter, MI (US); Haile Tecle, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 163 days.

(21) Appl. No.: 10/315,654

(22) Filed: Dec. 10, 2002

(65) Prior Publication Data

US 2003/0149015 A1 Aug. 7, 2003

Related U.S. Application Data

(62) Division of application No. 09/931,596, filed on Aug. 16, 2001, now Pat. No. 6,492,363, which is a division of application No. 09/462,319, filed as application No. PCT/US98/13105 on Jun. 24, 1998, now Pat. No. 6,310,060.

(60) Provisional application No. 60/051,433, filed on Jul. 1, 1997.

(51) Int. Cl.
*A61K 31/5377* (2006.01)
*A61K 31/496* (2006.01)
*A61K 31/277* (2006.01)
*A61K 31/198* (2006.01)

(52) U.S. Cl. ............ 514/559; 514/235.8; 514/317; 514/326; 514/381; 514/524; 514/534; 514/567; 558/418; 548/254; 548/950; 546/210; 546/229; 544/392; 544/366; 560/19; 562/433; 562/456

(58) Field of Classification Search ............... 562/454, 562/433; 514/559, 235.8, 317, 326, 381, 514/524, 534, 567; 560/19; 558/418; 548/254, 548/950; 544/392, 366; 546/210, 229
See application file for complete search history.

(56) References Cited

U.S. PATENT DOCUMENTS

| | | | |
|---|---|---|---|
| 2,077,249 A | 4/1937 | Mietzsch et al. | |
| 3,852,333 A | 12/1974 | Fisher | |
| 4,962,119 A | 10/1990 | Boschelli et al. | |
| 5,155,110 A | 10/1992 | Connor et al. | |
| 5,525,625 A | 6/1996 | Bridges et al. | |
| 6,310,060 B1 * | 10/2001 | Barrett et al. | 514/231.2 |

FOREIGN PATENT DOCUMENTS

EP 401857 A2 12/1990
WO WO 89/03818 A1 5/1989
WO WO9837881 9/1998

OTHER PUBLICATIONS

Bekemeier, H. et al.; "Structure–Activity Relationship in Nonsteroidal Antiinflammatory Agents, Including Osar in Fenamate Derivatives"; Agent & Actions Supplements; Jul. 1, 1982; pp. 17–34.
Berner, N.H. et al.; "Substituted N–Phenylanthranilic Acid Hydrazides as Potential Antimalarial & Antimicrobial Agents"; Journal of Medicinal Chemistry; vol. 13; No. 3; 1970; pp. 552–554.
Acheson, R.M. et al.; "The Condensation of Acridone with Tertiary Aromatic Amines and the Ultraviolet Absorption Spectra of the Products"; Journal of the Chemical Society; 1956; pp. 484–489.
Ramanujam, P. et al.; "Antifungal Activity of Some N–Substituted Anthranilic Acid Derivatives"; Planta Medica; vol. 25; No. 1; 1974; pp. 43–46.
Chemical Abstracts; vol. 99; No. 19; Nov. 7, 1983. (Abstract attached).
Chemical Abstracts; vol. 77; No. 19; Nov. 6, 1972. (Abstract attached).
Chemical Abstracts; vol. 114; No. 19; May 13, 1991. (Abstract attached).
Chemical Abstracts 12$^{th}$ Collective Index; vol. 106–115; 1987–1991; pp. 14641cs (Abstract attached).
Chemical Abstracts; vol. 109; No. 17; Oct. 24, 1988 (Abstract attached).
Chemical Abstracts 12$^{th}$ Collective Index; vol. 106–115; 1987–1991; pp. 15109cs (Abstract attached).
Chemical Abstracts; vol. 101; No. 3; Jul. 16, 1984 (Abstract attached).

(Continued)

*Primary Examiner*—Johann Richter
*Assistant Examiner*—Ebenezer Sackey
(74) *Attorney, Agent, or Firm*—Peter C. Richardson; Bryan C. Zielinski; Galina M. Yakovleva

(57) ABSTRACT

Phenylamino benzoic acid, benzamides, and benzyl alcohol derivatives of the formula where $R_1$, $R_2$, $R_3$, $R_4$, $R_5$, and $R_6$ are hydrogen or substituent groups such as alkyl, and where $R_7$ is hydrogen or an organic radical, and Z is $COOR_7$, tetrazolyl, $CONR_6R_7$, or $CH_2OR_7$, are potent inhibitors of MEK and, as such, are effective in treating cancer and other proliferative diseases such as inflammation, psoriasis and restenosis, as well as stroke, heart failure, and immunodeficiency disorders.

11 Claims, No Drawings

OTHER PUBLICATIONS

Chemical Abstracts 11th Collective Index; vol. 96–105; 1982–1986; pp. 10688cs (Abstract attached).

Chemical Abstracts; vol. 83; No. 3; Jul. 21, 1975 (Abstract attached).

Chemical Abstracts 9th Collective Index; vol. 76–85; 1972–1976; pp. 6385cs (Abstract attached).

Boschelli, D.H., et al., "Conversion of Nsaids Into Balanced Dual Inhibitors of Cyclooxygenase and 5–Lipoxygenase", Bioorg. Med. Chem. Letters, 1992, pp 69–72, vol. 2, No. 1, Pergamon Press, Great Britain.

Boschelli, D.H., et al., "1,3,4–Oxadiazole, 1,3,4–Thiadiazole, and 1,2,4–Triazole Analogs of the Fenamates: In Vitro Inhibition of Cyclooxygenase and 5–Lipoxygenase Activities", J. Med. Chem., 1993, pp1802–1810, vol. 36.

Munshi A. G., et al., "Synthesis of Dihalogenated 5–Aminoacridine Derivatives", J. Indian Chem.Soc., 1957, pp 367–368, vol. 34, No. 5.

Polaczek M., et al., Rocz. Chem., 1936, pp 76–78, vol. 16.

\* cited by examiner

2-(4-BROMO OR 4-IODO PHENYLAMINO) BENZOIC ACID DERIVATIVES

This application is a Divisional application of U.S. Ser. No. 09/931,596 filed Aug. 16, 2001, now U.S. Pat. No. 6,492,363; which is a Divisional application of U.S. Ser. No. 09/462,319 filed Jan. 5, 2000, now U.S. Pat. No. 6,310,060; which was a 35 U.S.C. 371 application from PCT/US98/13105 filed Jun. 24, 1998, which claimed priority to U.S. Ser. No. 60/051,433, filed Jul. 1, 1997.

FIELD OF THE INVENTION

This invention provides benzoic acid and amide derivatives of anthranilic acids which inhibit certain dual specificity kinase enzymes involved in proliferative diseases such as cancer and restenosis.

BACKGROUND OF THE INVENTION

Proliferative diseases are caused by a defect in the intracellular signaling system, or the signal transduction mechanism of certain proteins. Cancer, for example, is commonly caused by a series of defects in these signaling proteins, resulting from a change either in their intrinsic activity or in their cellular concentrations. The cell may produce a growth factor that binds to its own receptors, resulting in an autocrine loop, which continually stimulates proliferation. Mutations or overexpression of intracellular signaling proteins can lead to spurious mitogenic signals within the cell. Some of the most common mutations occur in genes encoding the protein known as Ras, which is a G-protein that is activated when bound to GTP, and inactivated when bound to GDP.

The above mentioned growth factor receptors, and many other mitogenic receptors, when activated, lead to Ras being converted from the GDP-bound state to the GTP-bound state. This signal is an absolute prerequisite for proliferation in most cell types. Defects in this signaling system, especially in the deactivation of the Ras.GTP complex, are common in cancers, and lead to the signaling cascade below Ras being chronically activated.

Activated Ras leads in turn to the activation of a cascade of serine/threonine kinases. One of the groups of kinases known to require an active Ras.GTP for its own activation is the Raf family. These in turn activate MEK, (eg, $MEK_1$ and $MEK_2$) which then activates MAP kinase. Activation of MAP kinase by mitogens appears to be essential for proliferation, and constitutive activation of this kinase is sufficient to induce cellular transformation. Blockade of downstream Ras signaling, for example by use of a dominant negative Raf-1 protein, can completely inhibit mitogenesis, whether induced from cell surface receptors or from oncogenic Ras mutants. Although Ras is not itself a protein kinase, it participates in the activation of Raf and other kinases, most likely through a phosphorylation mechanism. Once activated, Raf and other kinases phosphorylate MEK on two closely adjacent serine residues, $S^{218}$ and $S^{222}$ in the case of MEK-1, which are the prerequisite for activation of MEK as a kinase. MEK in turn phosphorylates MAP kinase on both a tyrosine, $Y^{185}$, and a threonine residue, $T^{183}$, separated by a single amino acid. This double phosphorylation activates MAP kinase at least 100-fold, and it can now catalyze the phosphorylation of a large number of proteins, including several transcription factors and other kinases. Many of these MAP kinase phosphorylations are mitogenically activating for the target protein, whether it be another kinase, a transcription factor, or other cellular protein. MEK is also activated by several kinases other than Raf-1, including MEKK, and itself appears to be a signal integrating kinase. As far as is currently known, MEK is highly specific for the phosphorylation of MAP kinase. In fact, no substrate for MEK other than MAP kinase has been demonstrated to date, and MEK does not phosphorylate peptides based on the MAP kinase phosphorylation sequence, or even phosphorylate denatured MAP kinase. MEK also appears to associate strongly with MAP kinase prior to phosphorylating it, suggesting that phosphorylation of MAP kinase by MEK may require a prior strong interaction between the two proteins. Both this requirement and the unusual specificity of MEK are suggestive that it may have enough difference in its mechanism of action to other protein kinases that selective inhibitors of MEK, possibly operating through allosteric mechanisms rather than through the usual blockade of the ATP binding site, may be found.

This invention provides compounds which are highly specific inhibitors of the kinase activity of MEK. Both in enzyme assays and whole cells, the compounds inhibit the phosphorylation of MAP kinase by MEK, thus preventing the activation of MAP kinase in cells in which the Ras cascade has been activated. The results of this enzyme inhibition include a reversal of transformed phenotype of some cell types, as measured both by the ability of the transformed cells to grow in an anchorage-independent manner and by the ability of some transformed cell lines to proliferate independently of external mitogens.

The compounds provided by this invention are 2-(phenylamino) benzoic acid, tetrazole, ester, amide, and benzyl alcohol derivatives, in which the phenyl ring is substituted at the 4-position with bromo or iodo. U.S. Pat. No. 5,155,110 discloses a wide variety of fenamic acid derivatives, including certain 2-(phenylamino) benzoic acid derivatives, as anti-inflammatory agents. The reference fails to describe the compounds of this invention or their kinase inhibitory activity.

SUMMARY OF THE INVENTION

This invention provides 4-bromo and 4-iodo phenylamino benzoic acid derivatives which are selective MEK kinase inhibitors and as such are useful for treating proliferative diseases such as cancer, psoriasis, and restenosis. The compounds are defined by Formula I

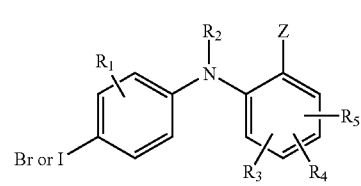

wherein:
$R_1$ is hydrogen, hydroxy, $C_1$–$C_8$ alkyl, $C_1$–$C_8$ alkoxy, halo, trifluoromethyl, or CN;
$R_2$ is hydrogen;
$R_3$, $R_4$, and $R_5$ independently are hydrogen, hydroxy, halo, trifluoromethyl, $C_1$–$C_8$ alkyl, $C_1$–$C_8$ alkoxy, nitro, CN, or —(O or NH)$_m$—(CH$_2$)$_n$—R$_9$, where $R_9$ is hydrogen, hydroxy, $CO_2H$, or $NR_{10}R_{11}$;
n is 0–4;
m is 0 or 1;
$R_{10}$ and $R_{11}$ independently are hydrogen or $C_1$–$C_8$ alkyl, or taken together with the nitrogen to which they are attached, can complete a 3–10 member cyclic ring optionally containing one, two, or three additional heteroatoms selected from O, S, NH, or N—$C_1$–$C_8$ alkyl;

Z is $COOR_7$, tetrazolyl, $CONR_6R_7$, $CONHNR_{10}R_{11}$, or $CH_2OR_7$;

$R_6$ and $R_7$ independently are hydrogen, $C_1$–$C_8$ alkyl, $C_2$–$C_8$ alkenyl, $C_2$–$C_8$ alkynyl,

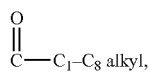

aryl, heteroaryl, $C_3$–$C_{10}$cycloalkyl, or $C_3$–$C_{10}$(cycloalkyl optionally containing one, two, or three heteroatoms selected from O, S, NH, or N alkyl); or $R_6$ and $R_7$ together with the nitrogen to which they are attached complete a 3–10 member cyclic ring optionally containing 1, 2, or 3 additional heteroatoms selected from O, S, NH, or N alkyl;

and wherein any of the foregoing alkyl, alkenyl, and alkynyl groups can be unsubstituted or substituted by halo, hydroxy, alkoxy, amino, alkylamino, dialkylamino, cycloalkyl, aryl, aryloxy, heteroaryl, or heteroaryloxy, and the pharmaceutically acceptable salts thereof.

Preferred compounds have Formula II

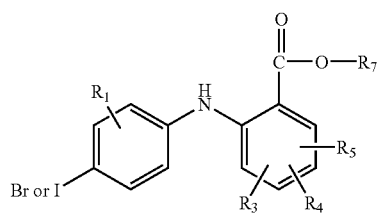

where $R_1$, $R_3$, $R_4$, $R_5$, $R_6$, and $R_7$ are as defined above. Especially preferred are compounds wherein $R_1$ is methyl or halo, and $R_3$, $R_4$, and $R_5$ are halo such as fluoro or bromo.

The compounds of Formula II are carboxylic acids when $R_7$ is hydrogen, and are esters when $R_7$ is other than hydrogen. Compounds which are analogous to the acids in physical and biological properties are tetrazolyl derivatives of Formula IIa

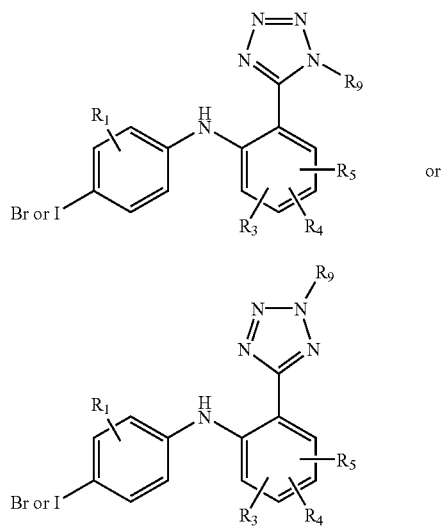

Another preferred group of compounds are amides Formula III

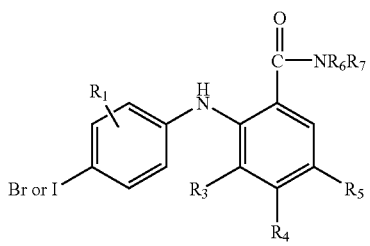

and hydrazides of Formula IIIa

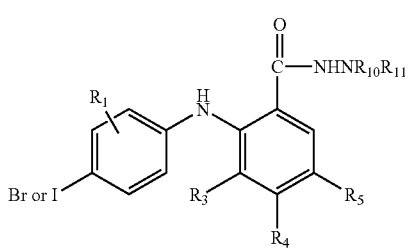

The benzyl alcohols of the invention have Formula IV

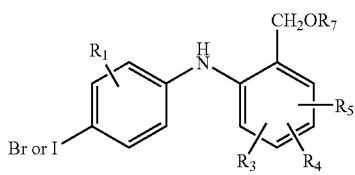

The most preferred compounds are those wherein $R_1$ is methyl, $R_3$ is hydrogen or halo such as fluoro, $R_4$ is halo such as fluoro, and $R_5$ is hydrogen or halo such as fluoro, bromo, or chloro. Representative compounds have the formulas

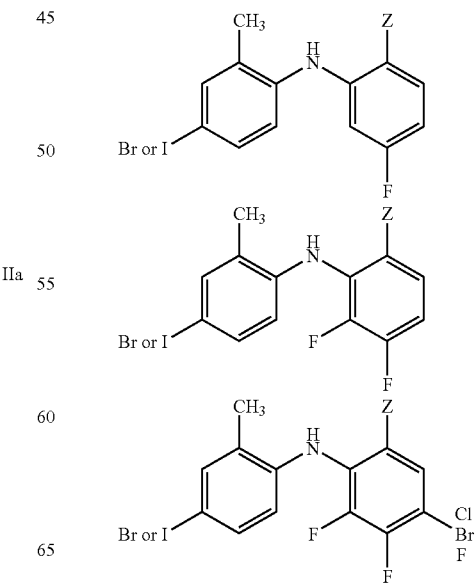

-continued

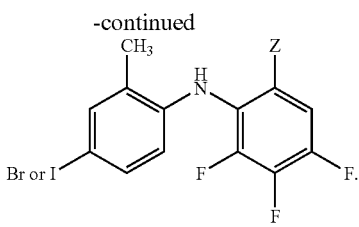

This invention also provides pharmaceutical formulations comprising a compound of Formula I together with a pharmaceutically acceptable excipient, diluent, or carrier. Preferred formulations include any of the foregoing preferred compounds together with an excipient, diluent, or carrier.

The compounds of Formula I are potent and selective inhibitors of $MEK_1$ and $MEK_2$ kinase enzymes. They are, therefore, useful to treat subjects suffering from cancer, stroke, diabetes, Alzheimer's disease, cystic fibrosis, viral disease, heart failure, and proliferative diseases such as psoriasis, restenosis, autoimmune disease, and atherosclerosis. The compounds are especially well suited to treat cancers such as breast cancer, colon cancer, prostate cancer, skin cancer, and pancreatic cancer. They are particularly well-suited for use in conjunction with conventional radiation therapy. The compounds are also immunomodulatory agents and can be used to treat degenerative diseases where change in MEK activation leads to pathologies such as hepatomegaly and cardiomegaly. The invention provides a method of inhibiting MEK enzymes and the foregoing diseases by administering to a subject an effective amount of a compound of Formula I.

DETAILED DESCRIPTION OF THE INVENTION

As used herein, the term "aryl" means a cyclic, bicyclic, or tricyclic aromatic ring moiety having from five to twelve carbon atoms. Examples of typical aryl groups include phenyl, naphthyl, and fluorenyl. The aryl may be substituted by one, two, or three groups selected from fluoro, chloro, bromo, iodo, alkyl, hydroxy, alkoxy, nitro, amino, alkylamino, or dialkylamino. Typical substituted aryl groups include 3-fluorophenyl, 3,5-dimethoxyphenyl, 4-nitronaphthyl, 2-methyl-4-chloro-7-aminofluorenyl, and the like.

The term "aryloxy" means an aryl group bonded through an oxygen atom, for example phenoxy, 3-bromophenoxy, naphthyloxy, and 4-methyl-1-fluorenyloxy.

"Heteroaryl" means a cyclic, bicyclic, or tricyclic aromatic ring moiety having from four to eleven carbon atoms and one, two, or three heteroatoms selected from O, S, or N. Examples include furyl, thienyl, pyrrolyl, pyrazolyl, imidazolyl, triazolyl, thiazolyl, oxazolyl, xanthenyl, pyronyl, indolyl, pyrimidyl, naphthyridyl, pyridyl, benzinnidazolyl, and triazinyl. The heteroaryl groups can be unsubstituted or substituted by one, two, or three groups selected from fluoro, chloro, bromo, iodo, alkyl, hydroxy, alkoxy, nitro, amino, alkylamino, or dialkylamino. Examples of substituted heteroaryl groups include chloropyranyl, methylthienyl, fluoropyridyl, amino-1,4-benzisoxazinyl, nitroisoquinolinyl, and hydroxyindolyl.

The heteroaryl groups can be bonded through oxygen to make heteroaryloxy groups, for example thienyloxy, isothiazolyloxy, benzofuranyloxy, pyridyloxy, and 4-methylisoquinolinyloxy.

The term "$C_1$–$C_8$ alkyl" means straight and branched chain aliphatic groups having from one to eight carbon atoms, preferably one to four. Typical $C_1$–$C_8$ alkyl groups include methyl, ethyl, isopropyl, tert.-butyl, 2,3-dimethylhexyl, and 1,1-dimethylpentyl. The alkyl groups can be unsubstituted or substituted by halo, hydroxy, alkoxy, amino, alkylamino, dialkylamino, cycloalkyl, aryl, aryloxy, heteroaryl, or heteroaryloxy, as those terms are defined herein. Typical substituted alkyl groups include chloromethyl, 3-hydroxypropyl, 2-dimethylaminobutyl, and 2-(hydroxymethylamino)ethyl. Examples of aryl and aryloxy substituted alkyl groups include phenylmethyl, 2-phenylethyl, 3-chlorophenylmethyl, 1,1-dimethyl-3-(2-nitrophenoxy)butyl, and 3,4,5-trifluoronaphthylmethyl. Examples of alkyl groups substituted by a heteroaryl or heteroaryloxy group include thienylmethyl, 2-furylethyl, 6-furyloxyoctyl, 4-methylquinolyloxymethyl, and 6-isothiazolylhexyl. Cycloalkyl substituted alkyl groups include cyclopropylmethyl, 2-cyclohexyethyl, piperidyl-2-methyl, 2-(piperidin-1-yl)-ethyl, 3-(morpholin-4-yl)propyl.

"$C_2$–$C_8$ Alkenyl" means a straight or branched carbon chain having one or more double bonds. Examples include but-2-enyl, 2-methyl-prop-2-enyl, 1,1-dimethyl-hex-4-enyl, 3-ethyl-4-methyl-pent-2-enyl, and 3-isopropyl-pent-4-enyl. The alkenyl groups can be substituted with halo, hydroxy, alkoxy, amino, alkylamino, dialkylamino, aryl, aryloxy, heteroaryl, or heteroyloxy, for example 2-bromoethenyl, 3-hydroxy-2-butenyl, 1-aminoethenyl, 3-phenylprop-2-enyl, 6-thienyl-hex-2-enyl, 2-furyloxy-but-2-enyl, and 4-naphthyloxy-hex-2-enyl.

"$C_2$–$C_8$ Alkynyl" means a straight or branched carbon chain having from two to eight carbon atoms and at least one triple bond. Typical alkynyl groups include prop-2-ynyl, 2-methyl-hex-5-ynyl, 3,4-dimethyl-hex-5-ynyl, and 2-ethyl-but-3-ynyl. The alkynyl groups can be substituted as the alkyl and alkenyl groups, for example, by aryl, aryloxy, heteroaryl, or heteroaryloxy, for example 4-(2-fluorophenyl)-but-3-ynyl, 3-methyl-5-thienylpent-4-ynyl, 3-phenoxy-hex-4-ynyl, and 2-furyloxy-3-methyl-hex-4-ynyl.

The alkenyl and alkynyl groups can have one or more double bonds or triple bonds, respectively, or a combination of double and triple bonds. For example, typical groups having both double and triple bonds include hex-2-en-4-ynyl, 3-methyl-5-phenylpent-2-en-4-ynyl, and 3-thienyloxy-hex-3-en-5-ynyl.

The term "$C_3$–$C_{10}$ cycloalkyl" means a nonaromatic ring or fused rings containing from three to ten carbon atoms. Examples include cyclopropyl, cyclobutyl, cyclopenyl, cyclooctyl, bicycloheptyl, adamantyl, and cyclohexyl. The ring can optionally contain one, two, or three heteroatoms selected from O, S, or $NR_9$. Such groups include tetrahydrofuryl, tetrahydropyrrolyl, octahydrobenzofuranyl, morpholinyl, piperazinyl, pyrrolidinyl, piperidinyl, octahydroindolyl, and octahydrobenzothiofuranyl. The cycloalkyl groups can be substituted with the same substituents as an alkyl and alkenyl groups, for example, halo, hydroxy, aryl, and heteroaryloxy. Examples include 3-hydroxycyclohexyl, 2-aminocyclopropyl, 2-phenylpyrrolidinyl, and 3-thienylmorpholine-1-yl.

$R_6$ and $R_7$ can be taken together with the nitrogen to which they are attached to complete a cyclic ring having from 3 to 10 members, which may contain 1, 2, or 3 additional heteroatoms selected from O, S, NH, or N alkyl. Examples of such cyclic rings include piperazinyl, piperidyl, pyrrolidinyl, morpholino, N-methylpiperazinyl, aziridynyl, and the like. Such rings can be substituted with halo, hydroxy, alkyl, alkoxy, amino, alkyl, and dialkylamino, aryl, aryloxy, heteroaryl, and heteroaryloxy. Typical examples include 3-hydroxy-pyrrolidinyl, 2-fluoro-piperindyl, 4-(2-hydroxyethyl)-piperidinyl, and 3-thienylmorpholino.

The 2-(4-bromo and 4-iodo phenylamino)-benzoic acid derivatives of Formula I can be prepared from commercially available starting materials utilizing synthetic methodologies well-known to those skilled in organic chemistry. A typical synthesis is carried out by reacting a 4-bromo or 4-iodo aniline with a benzoic acid having a leaving group at the 2-position to give a 2-(phenylamino)-benzoic acid. This process is depicted in Scheme 1.

Scheme 1

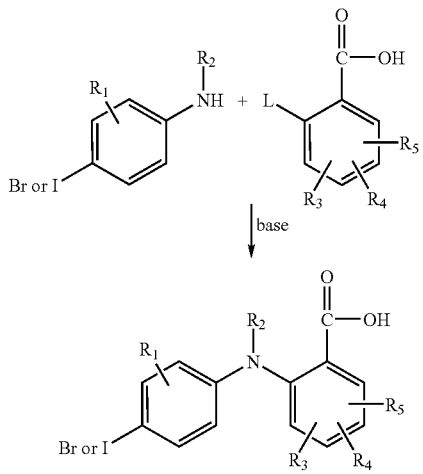

where L is a leaving group, for example halo such as fluoro.

The reaction of aniline and the benzoic acid derivative generally is accomplished by mixing the benzoic acid with an equimolar quantity or excess of the aniline in an unreactive organic solvent such as tetrahydrofuran or toluene, in the presence of a base such as lithium diisopropylamide, n-butyl lithium, sodium hydride, triethylamine, and Hunig's base. The reaction generally is carried out at a temperature of about $-78°$ C. to about $100°$ C., and normally is complete within about 2 hours to about 4 days. The product can be isolated by removing the solvent, for example by evaporation under reduced pressure, and further purified, if desired, by standard methods such as chromatography, crystallization, or distillation.

The 2-(phenylamino)-benzoic acid (eg, Formula I, where $R_7$ is hydrogen) can be reacted with an organic or inorganic base such as pyridine, triethylamine, calcium carbonate, or sodium hydroxide to produce a pharmaceutically acceptable salt. The free acids can also be reacted with an alcohol of the formula $HOR_7$ (where $R_7$ is other than hydrogen, for example methyl) to produce the corresponding ester. Reaction of the benzoic acid with an alcohol can be carried out in the presence of a coupling agent. Typical coupling reagents include 2-ethoxy-1-ethoxycarbonyl-1,2-dihydroquinoline (EEDQ), 1,3-dicyclohexylcarbodiimide (DCC), bromo-tris(pyrrolidino)-phosphonium hexafluorophosphate (PyBrOP), and (benzotriazolyloxy) tripyrrolidino phosphonium hexafluorophosphate (PyBOP). The phenylamino benzoic acid and alcohol derivative normally are mixed in approximately equimolar quantities in an unreactive organic solvent such as dichloromethane, tetrahydrofuran, chloroform, or xylene, and an equimolar quantity of the coupling reagent is added. A base such as triethylamine or diisopropylethylamine can be added to act as an acid scavenger if desired. The coupling reaction generally is complete after about 10 minutes to 2 hours, and the product is readily isolated by removing the reaction solvent, for instance by evaporation under reduced pressure, and purifying the product by standard methods such as chromatography or crystallizations from solvents such as acetone, diethyl ether, or ethanol.

The benzamides of the invention, Formula I where Z is $CONR_6R_7$, are readily prepared by reacting the foregoing benzoic acids with an amine of the formula $HNR_6R_7$. The reaction is carried out by reacting approximately equimolar quantities of the benzoic acid and amine in an unreactive organic solvent in the presence of a coupling reagent. Typical solvents are chloroform, dichloromethane, tetrahydrofuran, benzene, toluene, and xylene. Typical coupling reagents include DCC, EEDQ, PyBrOP, and PyBOP. The reaction is generally complete after about 10 minutes to about 2 hours when carried out at a temperature of about $0°$ C. to about $60°$ C. The product amide is readily isolated by removing the reaction solvent, for instance by evaporation, and further purification can be accomplished by normal methods such as chromatography, crystallization, or distillation. The hydrazides ($z=CONHNR_{10}R_{11}$) are similarly prepared by coupling a benzoic acid with a hydrazine of the formula $H_2HNR_{10}R_{11}$.

The benzyl alcohols of the invention, compounds of Formula I where Z is $CH_2OR_6$ and $R_6$ is hydrogen, are readily prepared by reduction of the corresponding benzoic acid according to the following scheme

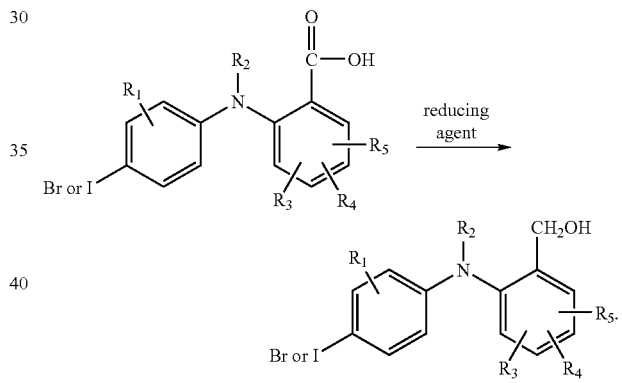

Typical reducing agents commonly employed include borane in tetrahydrofuran. The reduction normally is carried out in an unreactive organic solvent such as tetrahydrofuran, and generally is complete within about 2 hours to about 24 hours when conducted at a temperature of about $0°$ C. to about $40°$ C.

The following detailed examples illustrate specific compounds provided by this invention.

EXAMPLE 1

4-Fluoro-2-(4-iodo-2-methylphenylamino)benzoic Acid

To a stirring solution comprised of 3.16 g (0.0133 mol) of 2-amino-5-iodotoluene in 5 mL of tetrahydrofuran at $-78°$ C. was added 10 mL (0.020 mol) of a 2.0 M lithium diisopropylamide in tetrahydrofuran/heptane/ethenylbenzene (Aldrich) solution. The resulting green suspension was stirred vigorously for 15 minutes, after which time a solution of 1.00 g (0.00632 mol) of 2,4-difluorobenzoic acid in 10 mL of tetrahydrofuran was added. The reaction temperature was allowed to increase slowly to room temperature, at which temperature it was stirred for 2 days. The reaction mixture was concentrated. Aqueous HCl (10%) was added to the concentrate, and the solution was extracted with dichloromethane. The organic phase was dried (MgSO$_4$) and then boiled over a steambath to low volume and cooled to room temperature. The off-white fibers were collected by vacuum filtration, rinsed with hexanes, and vacuum-oven dried. (76° C.; ca. 10 mm of Hg) to afford 1.10 g (47%) of the desired material; mp 224–229.5° C.;

$^1$H NMR (400 MHz; DMSO): Λ 9.72 (s, 1H), 7.97 (dd, 1H, J=7.0, 8.7 Hz), 7.70 (d, 1H, J=1.5 Hz), 7.57 (dd, 1H, J=8.4, 1.9 Hz), 7.17 (d, 1H, J=8.2 Hz), 6.61–6.53 (m, 2H), 2.18 (s, 3H); $^{13}$C NMR (100 MHz; DMSO): Λ 169.87, 167.60, 165.12, 150.17, 150.05, 139.83, 138.49, 136.07, 135.31, 135.20, 135.07, 125.60, 109.32, 105.09, 104.87, 99.72, 99.46, 89.43, 17.52; $^{19}$F NMR (376 MHz; DMSO): δ–104.00 to –104.07 (m); IR (KBr) 1670 (C=0 stretch) cm$^{-1}$; MS (CI) M+1=372. Analysis calculated for C$_{14}$H$_{11}$FINO$_2$: C, 45.31; H, 2.99; N, 3.77. Found: C, 45.21; H, 2.77; N, 3.64.

EXAMPLES 2–30

By following the general procedure of Example 1, the following benzoic acids and salts were prepared:

| Example No. | Compound | MP ° C. |
|---|---|---|
| 2 | 3,4,5-Trifluoro-2-(4-iodo-2-methyl-phenylamino)-benzoic acid | 206–210 |
| 3 | 3,4-Difluoro-2-(4-iodo-2-methyl-phenylamino)-benzoic acid | 240.5–244.5 |
| 4 | 5-Bromo-3,4-difluoro-2-(4-iodo-2-methyl-phenylamino)-benzoic acid | 259.5–262 |
| 5 | 5-Chloro-2-(2-chloro-4-iodo-phenylamino)-benzoic acid | 255–260 |
| 6 | 5-Chloro-2-(4-iodo-2-methyl-phenylamino)-benzoic acid | 234–238 |
| 7 | Sodium 5-Chloro-2-(4-iodo-2-methyl-phenylamino)-benzoate | 310–320 DEC |
| 8 | 5-Bromo-2-(4-iodo-2-methyl-phenylamino)-benzoic acid | 239.5–240 |
| 9 | 2-(2-Chloro-4-iodo-phenylamino)-5-nitro-benzoic acid | 289–293 |
| 10 | 4-Fluoro-2-(3-fluoro-4-iodo-2-methyl-phenylamino)-benzoic acid | 233–235 |
| 11 | 2-(4-Iodo-methyl-phenylamino)-5-nitro-benzoic acid | 264–267 |
| 12 | 2-(2-Fluoro-4-iodo-phenylamino)-5-nitro-benzoic acid | 256–258 |
| 13 | 2-(4-Bromo-2-methyl-phenylamino)-4-fluoro-benzoic acid | 218.5–220 |
| 14 | 2-(2-Bromo-4-iodo-phenylamino)-5-nitro-benzoic acid | 285–288 DEC |
| 15 | 2-(4-Bromo-2-methyl-phenylamino)-3,4-difluoro-benzoic acid | 230–234 |
| 16 | 3-Fluoro-2-(4-iodo-2-methyl-phenylamino)-benzoic acid | 218–221 |
| 17 | 3,4-Difluoro-2-(4-iodo-2-methoxy-phenylamino)-benzoic acid | 230–233 |
| 18 | 4-Chloro-2-(4-iodo-2-methyl-phenylamino)-benzoic acid | 245–255 DEC |
| 19 | 2-(4-Iodo-2-methyl-phenylamino)-benzoic acid | 218–223 |
| 20 | 5-Fluoro-2-(4-iodo-2-methyl-phenylamino)-benzoic acid | 243–46 |
| 21 | 5-Iodo-2-(4-iodo-2-methyl-phenylamino)-benzoic acid | 241–245 |
| 22 | 2,3,5-Trifluoro-4-(4-iodo-2-methyl-phenylamino)-benzoic acid | 218–222 |
| 23 | 4-Fluoro-2-(3-chloro-4-iodo-2-methyl-phenylamino)-benzoic acid | 248–252.5 |
| 24 | 2-(4-Iodo-phenylamino)-5-methoxy-benzoic acid | 208–211 |
| 25 | 3-Chloro-2-(2-chloro-4-iodo-phenylamino)-benzoic acid | 232–233 |
| 26 | 2-Fluoro-6-(4-iodo-2-methyl-phenylamino)-benzoic acid | 179–182 |
| 27 | 4-Fluoro2-(2,3-dimethyl-4-iodo-2-methyl-phenylamino)-benzoic acid | 258–261 |
| 28 | 5-Methyl-2-(4-iodo-2-methyl-phenylamino)-benzoic acid | 209.5–211 |
| 29 | 2-Chloro-6-(4-iodo-2-methyl-phenylamino)-benzoic acid | 171–175 |
| 30 | 2-(4-Iodo-2-methyl-phenylamino)-4-nitro-benzoic acid | 251–263 |

EXAMPLE 31

5-Chloro-N-(2-hydroxyethyl)-2-(4-iodo-2-methyl-phenylamino)-benzamide

To a stirring solution comprised of 0.1020 g (0.2632 mmol) of 5-chloro-2-(4-iodo-2-methyl-phenylamino)-benzoic acid, 0.1 mL (1.7 mmol) of ethanolamine, and 0.05 mL (0.29 mmol) of diisopropylethylamine in 5 mL of a 1:1 (v/v) tetrahydrofuran-dichloromethane solution was added 0.15 g (0.29 mmol) of solid PyBOP powder directly. The reaction mixture was stirred at room temperature overnight. The solvent was removed in vacuo. The crude residue was partitioned between ether (50 mL) and 10% aqueous hydrochloric acid (50 mL). The organic phase was washed with 10% aqueous sodium hydroxide (50 mL), dried (MgSO$_4$) and concentrated in vacuo to afford a yellow-brown oil which was crystallized from hexanes-ether to afford 0.0831 g (73%) of a green-yellow powder; mp 120–121° C.;

$^1$H NMR (400 MHz; CDCl$_3$): δ 9.11 (s, 1H), 7.56 (d, 1H, J=1.4 Hz), 7.46–7.41 (m, 2H), 7.20 (dd, 1H, J=8.9, 2.4 Hz), 7.00 (t, 2H, J=9.6 Hz), 6.55 (broad t, 1H), 3.86 (t, 2H, J=5.0 Hz), 3.61 (dd, 2H, J=10.1, 5.5 Hz), 2.23 (s, 3H), 1.56 (broad s, 1H); IR (KBr) 3297 (O—H stretch), 1627 (C=O stretch) cm$^{-1}$; MS (CI) M+1=431. Analysis calculated for C$_{16}$H$_{16}$ClIN$_2$O$_2$: C, 44.62; H, 3.74; N, 6.50. Found: C, 44.63; H, 3.67; N, 6.30.

EXAMPLES 32–48

By following the general procedure of Example 31, the following benzamides were prepared by reacting the corresponding benzoic acid with the corresponding amine.

| Example No. | Compound | MP ° C. |
|---|---|---|
| 32 | 4-Methoxy-N-(4-methoxy-phenyl)-3-nitro-benzamide | 153.5–156 |
| 33 | 4-Fluoro-2-(4-iodo-2-methyl-phenylamino)-benzamide | 158 |
| 34 | 4-Fluoro-2-(4-iodo-2-methyl-phenylamino)-N-methyl-benzamide | 102.5–104.5 |
| 35 | N-Ethyl-4-fluoro-2-(4-iodo-2-methyl-phenylamino)-benzamide | 90–91 |
| 36 | 4-Fluoro-2-(4-iodo-2-methyl-phenylamino)-N,N-dimethyl-benzamide | oil |
| 37 | 4-Fluoro-2-(4-iodo-2-methyl-phenylamino)-N-(1H-tetrazol-5-yl)-benzamide | 285–288 DEC |

-continued

| Example No. | Compound | MP ° C. |
|---|---|---|
| 38 | 5-Bromo-2-(4-iodo-2-methyl-phenylamino)-benzamide | 180–182 |
| 39 | 5-Chloro-2-(4-iodo-2-methyl-phenylamino)-N,N-dimethyl-benzamide | 137–138 |
| 40 | [5-Chloro-2-(4-iodo-2-methyl-phenylamino)-benzoylamino]-acetic acid | 170–173 |
| 41 | 4-Fluoro-2-(4-iodo-2-methyl-phenylamino)-N-propyl-benzamide | 69–71 |
| 42 | 5-Bromo-N-(2-hydroxy-ethyl)-2-(4-iodo-2-methyl-phenylamino)-benzamide | 132–133.4 |
| 43 | N,N-Diethyl-4-fluoro-2-(4-iodo-2-methyl-phenylamino)-benzamide | oil |
| 44 | 4-Fluoro-N-{3-[4-(2-hydroxy-ethyl)-piperazin-1-yl]-propyl}-2-(4-iodo-2-methyl-phenylamino)-benzamide | 122–124 |
| 45 | N,N-Diethyl-2-(4-iodo-2-methyl-phenylamino)-5-nitro-benzamide | 91–93 |
| 46 | N-Butyl-4-fluoro-2-(4-iodo-2-methyl-phenylamino)-benzamide | 97–99 |
| 47 | 5-Chloro-N,N-diethyl-2-(4-iodo-2-methyl-phenylamino)-benzamide | 118–120 |
| 48 | 5-Bromo-2-(4-iodo-2-methyl-phenylamino)-N,N-dimethyl-benzamide | 142.5–144 |

EXAMPLE 49

4-Fluoro-2-(4-iodo-2-methyl-phenylamino)-benzyl Alcohol

4-Fluoro-2-(4-iodo-2-methyl-phenylamino)-benzoic acid (0.50 g, 1.35 mmol) was dissolved in 6 mL (6 mmol) of cold 1.0 M borane-tetrahydrofuran complex in tetrahydrofuran solution. The reaction mixture was stirred under nitrogen atmosphere at room temperature overnight. The reaction was quenched with 80 mL of methanol. Concentration in vacuo produced a clear tan oil which was purified by MPLC. Elution with dichloromethane afforded 0.4285 g (89%) of a white solid; mp 99–100.5° C.;

$^1$H NMR (400 MHz; DMSO): δ 7.57 (d, 1H, J=1.7 Hz), 7.45 (dd, 1H, J=8.4, 1.9 Hz), 7.39 (s, 1H), 7.29 (t, 1H, J=7.5 Hz), 6.89 (d, 1H, J=8.4 Hz), 6.67–6.60 (m, 1H), 5.47 (t, 1H, J=5.5 Hz), 4.49 (d, 2H, 5.1 Hz), 2.14 (s, 3H); IR (KBr) 3372 (O—H stretch) cm$^{-1}$; MS (CI) M+1=358. Analysis calculated for $C_{14}H_{13}FINO$: C, 47.08; H, 3.67; N, 3.92. Found: C, 47.17; H, 3.75; N, 3.72.

EXAMPLE 50–52

The following benzyl alcohols were prepared by the general procedure of Example 49.

| Example No. | Compound | MP ° C. |
|---|---|---|
| 50 | [5-Chloro-2-(4-iodo-2-methyl-phenylamino)-phenyl]-methanol | 82–85 |
| 51 | [2-(4-Iodo-2-methyl-phenylamino)-5-nitro-phenyl]-methanol | 126.5–128.5 |
| 52 | [5-Bromo-2-(4-iodo-2-methyl-phenylamino)-phenyl]-methanol | 60.5–63.5 |

Several invention compounds of Formula I were prepared utilizing combinatorial synthetic techniques. The general procedure is as follows:

To a 0.8-mL autosampler vial in a metal block was added 40 μL of a 0.5 M solution of the acid in DMF and 40 μL of the reagent amine (2M solution in Hunig's base and 1 M in amine in DMF). A 0.5M solution of PyBrop was freshly prepared and 50 μL were added to the autosampler vial. The reaction was allowed to stand for 24 hours.

The reaction mixture was transferred to a 2-dram vial and diluted with 2 mL of ethyl acetate. The organic layer was washed with 3 mL of distilled water and the water layer washed again with 2 mL of ethyl acetate. The combined organic layers were allowed to evaporate to dryness in an open fume hood.

The residue was taken up in 2 mL of 50% acetonitrile in water and injected on a semi-prep reversed phase column (10 mm×25 cm, 5 μM spherical silica, pore size 115 A derivatized with C-18, the sample was eluted at 4.7 mL/min with a linear ramp to 100% acetonitrile over 8.5 minutes. Elution with 100% acetonitrile continued for 8 minutes). Fractions were collected by monitoring at 214 nM. The residue was dissolved in chloroform and transferred to a preweighed vial, evaporated, and weighed again to determine the yield.

EXAMPLES 53–206

The following compounds of Formula I were prepared by combinatorial methodology:

| Example No. | Compound | MS M-H |
|---|---|---|
| 53 | 5-Bromo-3,4-difluoro-N-(2-hydroxy-ethyl)-2-(4-iodo-2-methyl-phenylamino)-benzamide | 510 |
| 54 | N-(2,3-Dihydroxy-propyl)-3,4-difluoro-2-(4-iodo-2-methyl-phenylamino)-benzamide | 462 |
| 55 | 5-Bromo-3,4-difluoro-2-(4-iodo-2-methyl-phenylamino)-N-(2-piperidin-1-yl-ethyl)-benzamide | 577 |
| 56 | 3,4-Difluoro-N-(2-hydroxy-ethyl)-2-(4-iodo-2-methyl-phenylamino)-benzamide | 432 |
| 57 | N-(2,3-Dihydroxy-propyl)-4-fluoro-2-(4-iodo-2-methyl-phenylamino)-benzamide | 444 |
| 58 | 3,4-Difluoro-N-(3-hydroxy-propyl)-2-(4-iodo-2-methyl-phenylamino)-benzamide | 446 |
| 59 | 5-Bromo-3,4-difluoro-2-(4-iodo-2-methyl-phenylamino)-N-(2-pyrrolidin-1-yl-ethyl)-benzamide | 564 |
| 60 | 5-Bromo-3,4-difluoro-2-(4-iodo-2-methyl-phenylamino)-N-(2-pyridin-4-yl-ethyl)-benzamide | 571 |
| 61 | 4-Fluoro-N-(2-hydroxy-ethyl)-2-(4-iodo-2-methyl-phenylamino)-benzamide | 414 |
| 62 | 5-Bromo-N-(3-dimethylamino-propyl)-3,4-difluoro-2-(4-iodo-2-methyl-phenylamino)-benzamide | 551 |
| 63 | 5-Bromo-3,4-difluoro-2-(4-iodo-2-methyl-phenylamino)-N-(2-morpholin-4-yl-ethyl)-benzamide | 580 |
| 64 | 3,4-Difluoro-2-(4-iodo-2-methyl-phenylamino)-N-(2-morpholin-4-yl-ethyl)-benzamide | 501 |
| 65 | 3,4-Difluoro-2-(4-iodo-2-methyl-phenylamino)-N-(2-pyrrolidin-1-yl-ethyl)-benzamide | 485 |
| 66 | 3,4-Difluoro-2-(4-iodo-2-methyl-phenylamino)-N-(2-pyridin-4-yl-ethyl)-benzamide | 493 |
| 67 | N-(3-Dimethylamino-propyl)-3,4-difluoro-2-(4-iodo-2-methyl-phenylamino)-benzamide | 473 |
| 68 | N-Benzyl-4-fluoro-2-(4-iodo-2-methyl-phenylamino)-benzamide | 460 |
| 69 | 2-(4-Bromo-2-methyl-phenylamino)-3,4-difluoro-N-(2-hydroxy-ethyl)-benzamide | 384 |
| 70 | 4-Fluoro-2-(4-iodo-2-methyl-phenylamino)-N-(2-morpholin-4-yl-ethyl)-benzamide | 483 |
| 71 | 4-Fluoro-2-(4-iodo-2-methyl-phenylamino)-N-(3-piperidin-1-yl-propyl)-benzamide | 495 |
| 72 | 3,4-Difluoro-2-(4-iodo-2-methyl-phenylamino)-N-(3-piperidin-1-yl-propyl)-benzamide | 513 |
| 73 | 4-Fluoro-2-(4-iodo-2-methyl-phenylamino)-N-(2-thiophen-2-yl-ethyl)-benzamide | 480 |
| 74 | 4-Fluoro-2-(4-iodo-2-methyl-phenylamino)-N-(2-pyrrolidin-1-yl-ethyl)-benzamide | 467 |

-continued

| Example No. | Compound | MS M-H |
|---|---|---|
| 75 | 2-(4-Bromo-2-methyl-phenylamino)-3,4-difluoro-N-(2-morpholin-4-yl-ethyl)-benzamide | 453 |
| 76 | 5-Bromo-3,4-difluoro-2-(4-iodo-2-methyl-phenylamino)-N-pyridin-4-ylmethyl-benzamide | 557 |
| 77 | 3,4-Difluoro-2-(4-iodo-2-methyl-phenylamino)-N-pyridin-4-ylmethyl-benzamide | 479 |
| 78 | 2-(4-Bromo-2-methyl-phenylamino)-N-(3-dimethylamino-propyl)-3,4-difluoro-benzamide | 425 |
| 79 | 4-Fluoro-2-(4-iodo-2-methyl-phenylamino)-N-pyridin-4-ylmethyl-benzamide | 461 |
| 80 | 4-Fluoro-2-(4-iodo-2-methyl-phenylamino)-N-(2-pyridin-4-yl-ethyl)-benzamide | 475 |
| 81 | 2-(4-Bromo-2-methyl-phenylamino)-3,4-difluoro-N-(2-pyridin-4-yl-ethyl)-benzamide | 445 |
| 82 | 2-(4-Bromo-2-methyl-phenylamino)-3,4-difluoro-N-(3-hydroxy-propyl)-benzamide | 400 |
| 83 | 2-(4-Bromo-2-methyl-phenylamino)-3,4-difluoro-N-(2-pyrrolidin-1-yl-ethyl)-benzamide | 437 |
| 84 | 4-Fluoro-2-(4-iodo-2-methyl-phenylamino)-N-phenethyl-benzamide | 474 |
| 85 | 2-(4-Bromo-2-methyl-phenylamino)-3,4-difluoro-N-(2-thiophen-2-yl-ethyl)-benzamide | 450 |
| 86 | 2-(4-Bromo-2-methyl-phenylamino)-3,4-difluoro-N-pyridin-4-ylmethyl-benzamide | 431 |
| 87 | 2-(4-Bromo-2-methyl-phenylamino)-3,4-difluoro-N-phenethyl-benzamide | 444 |
| 88 | 2-(4-Bromo-2-methyl-phenylamino)-3,4-difluoro-N-(2-piperidin-1-yl-ethyl)-benzamide | 451 |
| 89 | 5-Chloro-N-{3-[4-(2-hydroxy-ethyl)-piperazin-1-yl]-propyl}-2-(4-iodo-2-methyl-phenylamino)-benzamide | 557* |
| 90 | 5-Fluoro-N-{3-[4-(2-hydroxy-ethyl)-piperazin-1-yl]-propyl}-2-(4-iodo-2-methyl-phenylamino)-benzamide | 541* |
| 91 | 2-(4-Iodo-2-methyl-phenylamino)-5-nitro-N-pyridin-4-yl methyl-benzamide | 487 |
| 92 | 5-Bromo-N-{3-[4-(2-hydroxy-ethyl)-piperazin-1-yl]-propyl}-2-(4-iodo-2-methyl-phenylamino)-benzamide | 601* |
| 93 | 5-Chloro-N-(2-diethylamino-ethyl)-2-(4-iodo-2-methyl-phenylamino)-benzamide | 486* |
| 94 | 5-Chloro-2-(4-iodo-2-methyl-phenylamino)-N-(2-piperidin-1-yl-ethyl)-benzamide | 497* |
| 95 | (3-Hydroxy-pyrrolidin-1-yl)-[2-(4-iodo-2-methyl-phenylamino)-5-nitro-phenyl]- | 466 |
| 96 | 5-Chloro-2-(4-iodo-2-methyl-phenylamino)-N-(2-pyrrolidin-1-yl-ethyl)-benzamide | 484* |
| 97 | 5-Bromo-N-(2-diethylamino-ethyl)-2-(4-iodo-2-methyl-phenylamino)-benzamide | 530* |
| 98 | N-{2-[Bis-(2-hydroxy-ethyl)-amino]-ethyl}-5-chloro-2-(4-iodo-2-methyl-phenylamino)-benzamide | 518* |
| 99 | N-{2-[Bis-(2-hydroxy-ethyl)-amino]-ethyl}-5-bromo-2-(4-iodo-2-methyl-phenylamino)-benzamide | 562* |
| 100 | [5-Bromo-2-(4-iodo-2-methyl-phenylamino)-phenyl]-(3-hydroxy-pyrrolidin-1-yl)- | 499 |
| 101 | 2-(4-Iodo-2-methyl-phenylamino)-5-nitro-benzoic acid phenethyl ester | 501 |
| 102 | N-{3-[4-(2-Hydroxy-ethyl)-piperazin-1-yl]-propyl}-2-(4-iodo-2-methyl-phenylamino)-benzamide | 568* |
| 103 | [5-Chloro-2-(4-iodo-2-methyl-phenylamino)-phenyl]-(3-hydroxy-pyrrolidin-1-yl)- | 455 |
| 104 | 5-Fluoro-2-(4-iodo-2-methyl-phenylamino)-N-pyridin-4-ylmethyl-benzamide | 460 |
| 105 | 5-Bromo-2-(4-iodo-2-methyl-phenylamino)-N-(2-pyrrolidin-1-yl-ethyl)-benzamide | 528* |
| 106 | 5-Bromo-2-(4-iodo-2-methyl-phenylamino)-N-(2-piperidin-1-yl-ethyl)-benzamide | 542* |
| 107 | 5-Fluoro-2-(4-iodo-2-methyl-phenylamino)-N-(2-pyrrolidin-1-yl-ethyl)-benzamide | 468* |
| 108 | 5-Chloro-N-(3-dimethylamino-propyl)-2-(4-iodo-2-methyl-phenylamino)-benzamide | 472* |
| 109 | N-{2-[Bis-(2-hydroxy-ethyl)-amino]-ethyl}-5-fluoro-2-(4-iodo-2-methyl-phenylamino)-benzamide | 502* |
| 110 | 5-Chloro-N-(3-hydroxy-propyl)-2-(4-iodo-2-methyl-phenylamino)-benzamide | 445* |
| 111 | 5-Chloro-N-(3-diethylamino-2-hydroxy-propyl)-2-(4-iodo-2-methyl-phenylamino)-benzamide | 516* |
| 112 | 5-Fluoro-2-(4-iodo-2-methyl-phenylamino)-N-(2-piperidin-1-yl-ethyl)-benzamide | 482* |
| 113 | 5-Bromo-N-(3-hydroxy-propyl)-2-(4-iodo-2-methyl-phenylamino)-benzamide | 489* |
| 114 | 5-Bromo-2-(4-iodo-2-methyl-phenylamino)-N-(3-piperidin-1-yl-propyl)-benzamide | 556* |
| 115 | N-{2-[Bis-(2-hydroxy-ethyl)-amino]-ethyl}-2-(4-iodo-2-methyl-phenylamino)-5-nitro-benzamide | 529* |
| 116 | 5-Chloro-2-(4-iodo-2-methyl-phenylamino)-N-(2-morpholin-4-yl-ethyl)-benzamide | 500* |
| 117 | 5-Chloro-N-(3-diethylamino-propyl)-2-(4-iodo-2-methyl-phenylamino)-benzamide | 500* |
| 118 | 5-Chloro-N-(2-diisopropylamino-ethyl)-2-(4-iodo-2-methyl-phenylamino)-benzamide | 514* |
| 119 | 5-Chloro-2-(4-iodo-2-methyl-phenylamino)-N-(3-piperidin-1-yl-propyl)-benzamide | 512* |
| 120 | 2-(4-Iodo-2-methyl-phenylamino)-5-nitro-N-(2-piperidin-1-yl-ethyl)-benzamide | 509* |
| 121 | 5-Bromo-2-(4-iodo-2-methyl-phenylamino)-N-(2-piperazin-1-yl-ethyl)-benzamide | 544* |
| 122 | N-(2-Diethylamino-ethyl)-5-fluoro-2-(4-iodo-2-methyl-phenylamino)-benzamide | 470* |
| 123 | 5-Bromo-N-(3-dimethylamino-propyl)-2-(4-iodo-2-methyl-phenylamino)-benzamide | 516* |
| 124 | N-(3-Hydroxy-propyl)-2-(4-iodo-2-methyl-phenylamino)-5-nitro-benzamide | 456* |
| 125 | 5-Fluoro-N-(3-hydroxy-propyl)-2-(4-iodo-2-methyl-phenylamino)-benzamide | 429* |
| 126 | N-(3-Diethylamino-propyl)-5-fluoro-2-(4-iodo-2-methyl-phenylamino)-benzamide | 484* |
| 127 | N-(3-Diethylamino-propyl)-2-(4-iodo-2-methyl-phenylamino)-5-nitro-benzamide | 511* |
| 128 | 5-Bromo-2-(4-iodo-2-methyl-phenylamino)-N-(2-morpholin-4-yl-ethyl)-benzamide | 544* |
| 129 | 2-(4-Iodo-2-methyl-phenylamino)-5-nitro-N-(3-piperidin-1-yl-propyl)-benzamide | 523* |
| 130 | [5-Fluoro-2-(4-iodo-2-methyl-phenylamino)-phenyl]-(3-hydroxy-pyrrolidin-1-yl)- | 439 |
| 131 | 5-Bromo-N-(2-diisopropylamino-ethyl)-2-(4-iodo-2-methyl-phenylamino)-benzamide | 558* |
| 132 | 5-Fluoro-2-(4-iodo-2-methyl-phenylamino)-N-(2-morpholin-4-yl-ethyl)-benzamide | 484* |
| 133 | 5-Fluoro-2-(4-iodo-2-methyl-phenylamino)-N-(3-piperidin-1-yl-propyl)-benzamide | 496* |
| 134 | [5-Fluoro-2-(4-iodo-2-methyl-phenylamino)-phenyl]-[4-(2-hydroxy-ethyl)-piperazin-1- | 482 |
| 135 | N-(3-Diethylamino-2-hydroxy-propyl)-5-fluoro-2-(4-iodo-2-methyl-phenylamino)-benzamide | 500* |
| 136 | [5-Chloro-2-(4-iodo-2-methyl-phenylamino)-benzoylamino]-acetic acid | 443 |
| 137 | 2-(4-Iodo-2-methyl-phenylamino)-5-nitro-N-(2-pyrrolidin-1-yl-ethyl)-benzamide | 495* |
| 138 | N-(3-Dimethylamino-propyl)-2-(4-iodo-2-methyl-phenylamino)-5-nitro-benzamide | 483* |
| 139 | N-(2-Diisopropylamino-ethyl)-5-fluoro-2-(4-iodo-2-methyl-phenylamino)-benzamide | 498* |
| 140 | 5-Fluoro-2-(4-iodo-2-methyl-phenylamino)-thiobenzoic acid S-phenethyl ester | 490 |
| 141 | 5-Chloro-2-(4-iodo-2-methyl-phenylamino)-thiobenzoic acid S-phenethyl ester | 506 |
| 142 | 5-Bromo-2-(4-iodo-2-methyl-phenylamino)-thiobenzoic acid S-benzyl ester | 536 |
| 143 | 2-(4-Iodo-2-methyl-phenylamino)-5-nitro-thiobenzoic acid S-benzyl ester | 503 |
| 144 | 5-Fluoro-2-(4-iodo-2-methyl-phenylamino)-thiobenzoic acid S-benzyl ester | 476 |
| 145 | 5-Chloro-2-(4-iodo-2-methyl-phenylamino)-thiobenzoic acid S-benzyl ester | 492 |
| 146 | N-Cyclopropyl-5-fluoro-2-(4-iodo-2-methyl-phenylamino)-benzamide | 409 |
| 147 | 5-Chloro-N-(2-hydroxy-ethyl)-2-(4-iodo-2-methyl-phenylamino)-benzamide | 429 |
| 148 | 5-Fluoro-N-(2-hydroxy-ethyl)-2-(4-iodo-2-methyl-phenylamino)-benzamide | 413 |

| Example No. | Compound | MS M-H |
|---|---|---|
| 149 | N-Benzyloxy-5-fluoro-2-(4-iodo-2-methyl-phenylamino)-benzamide | 475 |
| 150 | N-Benzyloxy-5-bromo-2-(4-iodo-2-methyl-phenylamino)-benzamide | 593* |
| 151 | 2-(4-Iodo-2-methyl-phenylamino)-5-nitro-N-(4-sulfamoyl-benzyl)-benzamide | 567 |
| 152 | 5-Bromo-N-(2-hydroxy-ethyl)-2-(4-iodo-2-methyl-phenylamino)-benzamide | 473 |
| 153 | N-(2-Hydroxy-ethyl)-5-iodo-2-(4-iodo-2-methyl-phenylamino)-benzamide | 521 |
| 154 | N-(2-Hydroxy-ethyl)-2-(4-iodo-2-methyl-phenylamino)-5-nitro-benzamide | 440 |
| 155 | 2-(4-Iodo-2-methyl-phenylamino)-N-methyl-5-nitro-N-phenyl-benzamide | 486 |
| 156 | 5-Chloro-N-cyclopropyl-2-(4-iodo-2-methyl-phenylamino)-benzamide | 425 |
| 157 | 5-Fluoro-2-(4-iodo-2-methyl-phenylamino)-N-methyl-N-phenyl-benzamide | 459 |
| 158 | N-Allyl-5-fluoro-2-(4-iodo-2-methyl-phenylamino)-benzamide | 409 |
| 159 | N-Benzyloxy-5-iodo-2-(4-iodo-2-methyl-phenylamino)-benzamide | 583 |
| 160 | 5-Fluoro-2-(4-iodo-2-methyl-phenylamino)-N-(4-sulfamoyl-benzyl)-benzamide | 538 |
| 161 | N-Allyl-5-chloro-2-(4-iodo-2-methyl-phenylamino)-benzamide | 425 |
| 162 | N-Cyclopropyl-2-(4-iodo-2-methyl-phenylamino)-5-nitro-benzamide | 436 |
| 163 | 5-Bromo-N-cyclopropyl-2-(4-iodo-2-methyl-phenylamino)-benzamide | 469 |
| 164 | 5-Chloro-2-(4-iodo-2-methyl-phenylamino)-N-methyl-N-phenyl-benzamide | 475 |
| 165 | 5-Iodo-2-(4-iodo-2-methyl-phenylamino)-N-(4-sulfamoyl-benzyl)-benzamide | 646 |
| 166 | 5-Bromo-2-(4-iodo-2-methyl-phenylamino)-N-(4-sulfamoyl-benzyl)-benzamide | 598 |
| 167 | N-Allyl-2-(4-iodo-2-methyl-phenylamino)-5-nitro-benzamide | 436 |
| 168 | 2-(4-Iodo-2-methyl-phenylamino)-5-nitro-N-(4-sulfamoyl-benzyl)-benzamide | 565 |
| 169 | N-Allyl-5-bromo-2-(4-iodo-2-methyl-phenylamino)-benzamide | 469 |
| 170 | 5-Fluoro-2-(4-iodo-2-methyl-phenylamino)-N-(3-methyl-benzyl)-benzamide | 473 |
| 171 | N-Cyclopropyl-5-iodo-2-(4-iodo-2-methyl-phenylamino)-benzamide | 517 |
| 172 | 5-Bromo-2-(4-iodo-2-methyl-phenylamino)-N-methyl-N-phenyl-benzamide | 519 |
| 173 | N-Benzyloxy-2-(4-iodo-2-methyl-phenylamino)-5-nitro-benzamide | 502 |
| 174 | N-Cyclohexyl-5-iodo-2-(4-iodo-2-methyl-phenylamino)-benzamide | 559 |
| 175 | N-Allyl-5-iodo-2-(4-iodo-2-methyl-phenylamino)-benzamide | 517 |
| 176 | 5-Iodo-2-(4-iodo-2-methyl-phenylamino)-N-(3-methyl-benzyl)-benzamide | 581 |
| 177 | 2-(4-Iodo-2-methyl-phenylamino)-N-(3-methyl-benzyl)-5-nitro-benzamide | 500 |
| 178 | 5-Iodo-2-(4-iodo-2-methyl-phenylamino)-N-methyl-N-phenyl-benzamide | 567 |
| 179 | N-Cyclohexyl-5-fluoro-2-(4-iodo-2-methyl-phenylamino)-benzamide | 451 |
| 180 | 5-Chloro-N-cyclohexyl-2-(4-iodo-2-methyl-phenylamino)-benzamide | 467 |
| 181 | 5-Bromo-2-(4-iodo-2-methyl-phenylamino)-N-(3-methyl-benzyl)-benzamide | 533 |
| 182 | 5-Bromo-N-cyclohexyl-2-(4-iodo-2-methyl-phenylamino)-benzamide | 511 |
| 183 | 5-Chloro-2-(4-iodo-2-methyl-phenylamino)-N-(3-methyl-benzyl)-benzamide | 489 |
| 184 | N-Cyclohexyl-2-(4-iodo-2-methyl-phenylamino)-5-nitro-benzamide | 478 |
| 185 | N-Benzyloxy-5-bromo-2-(4-iodo-2-methyl-phenylamino)-benzamide | 538 |
| 186 | N-Benzyloxy-5-fluoro-2-(4-iodo-2-methyl-phenylamino)-benzamide | 477 |
| 187 | 5-Chloro-N-(2-hydroxy-ethyl)-2-(4-iodo-2-methyl-phenylamino)-benzamide | 431 |
| 188 | 5-Bromo-N-(2-hydroxy-ethyl)-2-(4-iodo-2-methyl-phenylamino)-benzamide | 475 |
| 189 | 2-(4-Iodo-2-methyl-phenylamino)-N-methyl-5-nitro-N-phenyl-benzamide | 488 |
| 190 | 5-Chloro-2-(4-iodo-2-methyl-phenylamino)-N-methyl-N-phenyl-benzamide | 477 |
| 191 | N-(2-Hydroxy-ethyl)-5-iodo-2-(4-iodo-2-methyl-phenylamino)-benzamide | 523 |
| 192 | 5-Chloro-N-cyclopropyl-2-(4-iodo-2-methyl-phenylamino)-benzamide | 425 |
| 193 | N-Allyl-5-chloro-2-(4-iodo-2-methyl-phenylamino)-benzamide | 427 |
| 194 | 5-Fluoro-2-(4-iodo-2-methyl-phenylamino)-N-methyl-N-phenyl-benzamide | 461 |
| 195 | N-(2-Hydroxy-ethyl)-2-(4-iodo-2-methyl-phenylamino)-5-nitro-benzamide | 442 |
| 196 | 5-Fluoro-N-(2-hydroxy-ethyl)-2-(4-iodo-2-methyl-phenylamino)-benzamide | 415 |
| 197 | 5-Bromo-N-cyclopropyl-2-(4-iodo-2-methyl-phenylamino)-benzamide | 472 |
| 198 | N-Cyclopropyl-5-fluoro-2-(4-iodo-2-methyl-phenylamino)-benzamide | 411 |
| 199 | 5-Fluoro-2-(4-iodo-2-methyl-phenylamino)-N-(4-sulfamoyl-benzyl)-benzamide | 540 |
| 200 | N-Cyclopropyl-2-(4-iodo-2-methyl-phenylamino)-5-nitro-benzamide | 438 |
| 201 | N-Allyl-5-fluoro-2-(4-iodo-2-methyl-phenylamino)-benzamide | 411 |
| 202 | N-Benzyloxy-5-iodo-2-(4-iodo-2-methyl-phenylamino)-benzamide | 585 |
| 203 | N-Allyl-5-bromo-2-(4-iodo-2-methyl-phenylamino)-benzamide | 472 |
| 204 | 5-Bromo-2-(4-iodo-2-methyl-phenylamino)-N-(4-sulfamoyl-benzyl)-benzamide | 601 |
| 205 | 5-Bromo-2-(4-iodo-2-methyl-phenylamino)-N-methyl-N-phenyl-benzamide | 522 |
| 206 | N-Allyl-2-(4-iodo-2-methyl-phenylamino)-5-nitro-benzamide | 438 |

*M + H

EXAMPLE 207

Preparation of [4-Chloro-2-(1H-tetrazol-5-yl)-(4-iodo-2-methyl-phenyl)-amine

Step a: Preparation of 5-Chloro-2-fluoro-benzaldehyde

To a solution of 1-chloro-4-fluorobenzne (13.06 g, 0.1 mol) in THF (180 mL), at −78° C., LDA (2 M solution in THF, 50 mL, 0.1 mol) was added dropwise. After stirring at −78° C. for 1.5 hours, DMF (8 mL) was added to the reaction mixture and allowed to warm up to room temperature overnight. The reaction mixture was partitioned between water and $Et_2O$. The $Et_2O$ layer was dried ($MgSO_4$) and the solvent removed in vacuum to give 14.95 g (94%) yield of crude aldehyde:

$^1$H NMR ($CDCl_3$): δ, 10.3 (s, —C(=O)H).

Step b: Preparation of 5-Chloro-2-fluoro-benzaldehyde oxime

A solution of 5-chloro-2-fluoro-benzaldehyde (10 g, 0.0631 mol), hydroxylamine hydrochloride (6.57 g, 0.0946 mol) and pyridine (8.3 mL, 0.1010 mol) in EtOH (100 mL) was heated at 75° C. (oil bath temperature) for 1 hour and the solvent removed under vacuum to give an oil. The oil was partitioned between water and $CH_2Cl_2$. The $CH_2Cl_2$ layer was dried ($MgSO_4$) and the solvent removed under vacuum to give crude aldoxime as a solid. The solid was purified by medium pressure liquid chromatography on silica. Elution with $CH_2Cl_2$ gave 4.87 g (28%) of the aldoxime as white solid: mp 95–97° C.;

Analysis calculated for $C_7H_5NOFCl$: C, 48.44; H, 2.90; N, 8.07. Found: C, 48.55; H, 2.69, N, 7.90.

Step c: Preparation of 5-Chloro-2-fluoro-benzonirile

A solution of the 5-chloro-2-fluoro-benzaldehyde oxime (3.15 g, 0.0182 mol) in acetic anhydride (150 mL) was refluxed for 16 hours. The reaction mixture was cooled to room temperature and poured into saturated aqueous $NaHCO_3$ (200 mL) solution. The mixture was extracted with $Et_2O$. The $Et_2O$ layer was dried ($K_2CO_3$) and the solvent removed to give the product as an oily solid. The product was used without further purification in the next step.

Step d: Preparation of 5-(5-Chloro-2-fluoro-phenyl)-1H-tetrazole

A mixture of 5-chloro-2-fluoro-benzonitrile (2.84 g, 0.01823 mol), butanol (15 mL), sodium azide (1.543 g, 0.0237 mol), acetic acid (1.36 mL, 0.0237 mol) was refluxed for 24 hours. The reaction mixture was cooled to room temperature, additional 1.543 g sodium azide added, and the reaction mixture refluxed for additional 24 hours. After cooling to room temperature, $Et_2O$ (100 mL) and 10% aqueous NaOH (200 mL) were added sequentially. The mixture was vigorously stirred. The aqueous layer was separated, cooled with ice-methanol bath (−15° C.) and acidified to pH 1 with conc. HCl. A gray solid precipitated. The solid was dried in vacuum at 50° C. to give 1.76 g (49%) of 5-(5-chloro-2-fluoro-phenyl)-1H-tetrazole: mp partial melt at 110° C., complete melting at 124° C.);

$^1$H (400 Mz, $CDCl_3$): δ 8.19–8.08 (m, 1H), 7.77–7.71 (m, 1H), 7.61–7.52 (m, 1H); $^{13}$C (100 Mz, $CDCl_3$): δ 159.00, 156.49, 140.88, 133.02, 132.93, 130.73, 129.23, 129.21, 129.08, 126.05, 118.96, 118.73, 114.50; MS (CI) M+1=199 (100), M=198 (6).

Step e: Preparation of [4-Chloro-2-(1H-tetrazol-5-yl)-(4-iodo-2-methyl-phenyl)-amine To a solution of 2-methyl-4-iodoaniline (3.52 g, 0.0151 mol) in THF (25 mL) at −78° C., LDA (2 molar solution in THF, 11.33 mL, 0.02267 mol) was added dropwise. After stirring for 0.5 hours, a solution of 1-(tetrazol-5-yl)-2-fluoro-5-chlorobenzene (1.5 g, 0.00756 mol) in THF (15 mL) was added dropwise. The reaction was stirred for 16 hours as it warmed up to room temperature. The reaction mixture was quenched with aqueous conc. $NH_4Cl$ solution and extracted with $CH_2Cl_2$. The organic layer was dried ($MgSO_4$) and the solvent removed giving a crude product as an oil. The oil with $CH_2Cl_2$->$CH_2Cl_2$:MeOH (9.7:0.3) gave 1.5 g (48%) of the desired product: mp 205–208;

$^1$H (400 Mz, DMSO): δ 9.13 (s, 1H), 8.00–7.99 (s, 1H), 7.69 (s, 1H), 7.55–7.52 (m, 1H), 7.43–7.40 (m, 1H), 7.12–7.05 (m, 1H), 2.24 (s, 3H); $^{13}$C (100 Mz, $CDCl_3$): δ 141.87, 139.28, 138.88, 135.47, 133.71, 131.65, 128.15, 123.69, 121.94, 116.68, 87.79, 17.22; MS (CI) M+2=413 (44), M+1=412 (85), M=411 (100). Analysis calculated for $C_{14}H_{11}N_5Cl I.0.5H_2O$: C, 39.97; H, 2.87; N, 16.65. Found: C, 38.87, H, 2.77; N, 16.47.

The following tetrazole substituted phenylamines were prepared by following the general procedure of Example 207.

EXAMPLE 208

(4-Iodo-2-methyl-phenyl)-[2-(1H-tetrazol-5-yl)-phenyl]amine, mp 231° C. (dec)

EXAMPLE 209

[4-Nitro-2-(1H-tetrazol-5-yl)-(4-iodo-2-methyl-phenyl)-amine, mp 205–208° C.

The invention compounds are useful in treating cancer and other proliferative diseases by virtue of their selective inhibition of the dual specificity protein kinases $MEK_1$ and $MEK_2$. The invention compound has been evaluated in a number of biological assays which are normally utilized to establish inhibition of proteins and kinases, and to measure mitogenic and metabolic responses to such inhibition.

EXAMPLES 210–224

Additional invention compounds which were prepared by the general methods described above are:

| Example No. | Compound | MP ° C. |
|---|---|---|
| 210 | 2-(2-Chloro-4-iodo-phenylamino)-3-fluoro-4-(2-morpholin-4-yl-ethylamino)-5-nitro-benzoic acid | 239–241 DEC |
| 211 | 4-Amino-2-(2-chloro-4-iodo-phenylamino)-3-fluoro-5-nitro-benzoic acid | >270 |
| 212 | 2,4-Bis-(2-chloro-4-iodo-phenylamino)-3-fluoro-5-nitro-benzoic acid | >265 DEC |
| 213 | 4-Fluoro-2-(4-iodo-2-methyl-phenylamino)-5-nitro-benzoic acid | 218–225 DEC |
| 214 | 2-(2,6-Difluoro-4-iodo-phenylamino)-3,4-difluoro-benzoic acid | 247–249 |
| 215 | 2-(2-Chloro-4-iodo-phenylamino)-4-nitro-benzoic acid | 267–269 |
| 216 | 2-(2,4-Diiodo-phenylamino)-4-fluoro-benzoic acid | 260–261 |
| 217 | 2-(2-Bromo-4-iodo-phenylamino)-4-fluoro-benzoic acid | 259–262 |
| 218 | 4-Fluoro-2-(2-fluoro-4-iodo-phenylamino)-benzoic acid | 215–217 |
| 219 | 2-(2-Chloro-4-iodo-phenylamino)-4-fluoro-benzoic acid | 242–247 |
| 220 | 5-Bromo-2-(2-chloro-4-iodo-phenylamino)-3,4-difluoro-benzoic acid | 312.5–318 |
| 221 | 2,3,5-Trifluoro-6-(4-iodo-2-methyl-phenylamino)-4-(4-methyl-piperazin-1-yl)-benzoic acid methyl ester dihydrofluoride salt | 118–121 |
| 222 | 5-Bromo-3,4-difluoro-2-(4-iodo-2-methyl-phenylamino)-N-(4-methyl-piperazin-1-yl)-benazmide | 214–217 DEC |
| 223 | 5-Bromo-3,4-difluoro-2-(4-iodo-2-methyl-phenylamino)-benzoic acid N',N'-dimethyl-hydrazide | 154–175 DEC |
| 224 | 4-Fluoro-2-(4-iodo-2-methyl-phenylamino)-benzoic acid hydrazide | 153.5–156 |

Enzyme Assays

Cascade Assay for Inhibitors of the MAP Kinase Pathway

Incorporation of $^{32}$P into myelin basic protein (MBP) was assayed in the presence of a glutathione S-transferase fusion protein containing p44MAP kinase (GST-MAPK) and a glutathione S-transferase fusion protein containing p45MEK (GST-MEK). The assay solution contained 20 mM HEPES, pH 7.4, 10 mM $MgCl_2$, 1 mM $MnCl_2$, 1 mM EGTA, 50 μM [γ-$^{32}$P]ATP, 10 μg GST-MEK, 0.5 μg GST-MAPK and 40 μg MBP in a final volume of 100 μL. Reactions were stopped after 20 minutes by addition of trichloroacetic acid and filtered through a GF/C filter mat. $^{32}$P retained on the filter mat was determined using a 1205 Betaplate. Compounds were assessed at 10 μM for ability to inhibit incorporation of $^{32}$P.

To ascertain whether compounds were inhibiting GST-MEK or GST MAPK, two additional protocols were employed. In the first protocol, compounds were added to tubes containing GST-MEK, followed by addition of GST-MAPK, MBP and [γ-$^{32}$P]ATP. In the second protocol, compounds were added to tubes containing both GST-MEK and GST-MAPK, followed by MBP and [γ-$^{32}$P]ATP. Compounds that showed activity in both protocols were scored as MAPK inhibitors, while compounds showing activity in only the first protocol were scored as MEK inhibitors.

In Vitro MAP Kinase Assay

Inhibitory activity was also confirmed in direct assays. For MAP kinase, 1 μg GST-MAPK was incubated with 40 μg MBP for 15 minutes at 30° C. in a final volume of 50 μL containing 50 mM Tris (pH 7.5), 10 μM MgCl$_2$, 2 μM EGTA, and 10 μM [γ-$^{32}$P]ATP. The reaction was stopped by addition of Laemmli SDS sample buffer and phosphorylated MBP resolved by electrophoresis on a 10% polyacrylamide gel. Radioactivity incorporated into MBP was determined by autoradiography, and subsequently by excision of the bands followed by scintillation counting.

In Vitro MEK Assay

For evaluation of direct MEK activity, 10 μg GST-MEK$_1$ was incubated with 5 μg of a glutathione S-transferase fusion protein containing p44MAP kinase with a lysine to alanine mutation at position 71 (GST-MAPK-KA). This mutation eliminates kinase activity of MAPK, so only kinase activity attributed to the added MEK remains. Incubations were 15 minutes at 30° C. in a final volume of 50 μL containing 50 mM Tris (pH 7.5), 10 μM MgCl$_2$, 2 μM EGTA, and 10 μM [γ-$^{32}$P]ATP. The reaction was stopped by addition of Laemmli SDS sample buffer and phosphorylated GST-MAPK-KA was resolved by electrophoresis on a 10% polyacrylamide gel. Radioactivity incorporated into GST-MAPK-KA was determined by autoradiography, and subsequently by excision of the bands followed by scintillation counting. Additionally, an artificially activated MEK was utilized that contained serine to glutamate mutations at positions 218 and 222 (GST-MEK-2E). When these sites are phosphorylated, MEK activity is increased. Phosphorylation of these sites can be mimicked by mutation of the serine residues to glutamate. For this assay, 5 μg GST-MEK-2E was incubated with 5 μg GST-MAPK-KA for 15 minutes at 30° C. in the same reaction buffer as described above. Reactions were terminated and analyzed as above.

Whole Cell MAP Kinase Assay

To determine if compounds were able to block activation of MAP kinase in whole cells, the following protocol was used: Cells were plated in multi-well plates and grown to confluence. Cells were then serum-deprived overnight. Cells were exposed to the desired concentrations of compound or vehicle (DMSO) for 30 minutes, followed by addition of a growth factor, for example, PDGF (100 ng/mL). After a 5-minute treatment with the growth factor, cells were washed with PBS, then lysed in a buffer consisting of 70 mM NaCl, 10 mM HEPES (pH 7.4), 50 mM glycerol phosphate, and 1% Triton X-100. Lysates were clarified by centrifugation at 13,000×g for 10 minutes. Five micrograms of the resulting supernatants were incubated with 10 μg microtubule associated protein-2 (Map2) for 15 minutes at 30° C. in a final volume of 25 μL containing 50 mM Tris (pH 7.4), 10 mM MgCl$_2$, 2 mM EGTA and 30 μM [γ-$^{32}$P]ATP. Reactions were terminated by addition of Laemmli sample buffer. Phosphorylated Map2 was resolved on 7.5% acrylamide gels and incorporated radioactivity determined by autoradiography and subsequent excision of the bands followed by scintillation counting.

Immunoprecipitation and Antiphosphotyrosine Immunoblots

To determine the state of tyrosine phosphorylation of cellular MAP kinase, cells were lysed, endogenous MAP kinase was immunoprecipitated with a specific antibody, and the resulting immunoprecipitate analyzed for the presence of phosphotyrosine as follows: confluent cells were serum-deprived overnight and treated with compounds and growth factors as described above. Cells were then scraped and pelleted at 13,000×g for 2 minutes. The resulting cell pellet was resuspended and dissolved in 100 μL of 1% SDS containing 1 mM NaVO$_4$. Following alternate boiling and vortexing to denature cellular protein, 900 μL RIPA buffer (50 mM Tris (pH 7.4), 150 mM NaCl, 1% Triton X-100, 0.1% deoxycholate, and 10 mM EDTA) was added. To this mixture was added 60 μL agarose beads coupled with rabbit immunoglobulin G and 60 μL Pansorbin cells in order to clear the lysate of nonspecific binding proteins. This mixture was incubated at 4° C. for 15 minutes then centrifuged at 13,000×g for 10 minutes. The resulting supernatant was transferred to fresh tubes and incubated with 10 μL of a polyclonal antisera raised against a fragment of MAP kinase for a minimum of 1 hour at 4° C. Seventy microliters of a slurry of agarose beads coupled with protein G and protein A was added and the incubation continued for an additional 30 minutes at 4° C. The beads were pelleted by centrifugation at 13,000×g for 5 minutes and washed three times with 1 mL RIPA buffer. Laemmli sample buffer was added to the final bead pellet. This mixture was boiled for 5 minutes then resolved on a 10% acrylamide gel. Proteins on the gel were transferred to a nitrocellulose membrane and nonspecific binding sites on the membrane blocked by incubation with 1% ovalbumin and 1% bovine serum albumin in TBST (150 mM NaCl, 10 mM Tris (pH 7.4), and 0.05% Tween 20). The membrane was then incubated with a commercially available antibody directed against phosphotyrosine. Antibody bound on the membrane was detected by incubation with $^{125}$I-protein A, followed by autoradiography.

Cell Growth Assays $^3$H-Thymidine Incorporation

Cells were plated in multi-well plates and grown to near confluence. The media was then removed and replaced with growth media containing 1% bovine serum albumin. After 24-hour serum starvation, compounds and specific growth factors were added and incubations continued for an additional 24 hours. During the final 2 hours, $^3$H-thymidine was added to the medium. To terminate the incubations, the medium was removed and cell layers washed twice with ice-cold phosphate-buffered saline. After the final wash, ice-cold 5% trichloroacetic acid was added and the cells incubated for 15 minutes at room temperature. The trichloroacetic acid solution was then removed and the cell layer washed three times with distilled water. After the final wash, the cell layer was solubilized by addition of 2% sodium dodecylsulfate. Radioactivity in this solution was determined by scintillation counting.

In 3T3-L1 adipocyte cells, in which the inhibition blocks MAPK activation by insulin with an IC$_{50}$ of 3 μM, the compound had no effect on the insulin stimulated uptake of radiolabeled 2-deoxyglucose, or on the insulin-stimulated synthesis of either lipid or glycogen at 10 μM concentration. This demonstrates that the inhibitor shows selectivity between the mitogenic and metabolic effects of insulin, and demonstrates that the inhibitor will show less toxicity than an inhibitor which does not show this surprising selectivity.

Monolayer Growth

Cells were plated into multi-well plates at 10 to 20,000 cells/mL. Forty-eight hours after seeding, compounds were added to the cell growth medium and incubation was continued for 2 additional days. Cells were then removed from the wells by incubation with trypsin and enumerated with a Coulter counter.

Growth in Soft-Agar

Cells were seeded into 35-mm dishes at 5 to 10,000 cells/dish using growth medium containing 0.3% agar. After chilling to solidify the agar, cells were transferred to a 37° C. incubator. After 7 to 10 days growth, visible colonies were manually enumerated with the aid of a dissecting microscope. Order of addition experiments established that the invention compounds are inhibiting MEK and not MAP kinase. Experiments looking at the phosphorylation of a kinase defective mutant of MAP kinase as substrate (so that there can be no autophosphorylation of the MAP kinase to complicate interpretation) confirms that the inhibitor inhibits MEK with an $IC_{50}$ essentially identical to that produced in the cascade assay.

Kinetic analysis demonstrates that the invention compounds are not competitive with ATP. Thus, they do not bind at the ATP binding site of the enzyme, which is probably the explanation as to why these compounds do not show the nonspecific kinase inhibitory activity typical of most kinase inhibitors, which do bind at the ATP binding site and which are ATP competitive. The in vitro and in vivo biological activity of several representative compounds of Formula I in the foregoing assays is presented in Table 1.

TABLE 1

| Compound of Example No. | In Vitro | | In Vivo (Cell Culture) | |
|---|---|---|---|---|
| | % Inhibition | $IC_{50}$ μM | % Inhibition | $IC_{50}$ μM |
| 1 | | 0.019 | | |
| 2 | | 0.014 | | 3 |
| 3 | | 0.0111 | | 10 |
| 4 | | 0.005 | | 1 |
| 5 | | 0.066 | | |
| 6 | | 0.071 | | |
| 7 | | 0.072 | | |
| 8 | | 0.086 | | |
| 9 | | 0.097 | | |
| 10 | | 0.101 | | |
| 11 | | 0.128 | | |
| 12 | | 0.135 | | |
| 13 | | 0.178 | | |
| 14 | | 0.179 | | |
| 15 | | 0.194 | | |
| 16 | | 0.323 | | |
| 17 | | 0.434 | | |
| 18 | | 0.446 | | |
| 19 | | 0.524 | 50% at 30 μM | |
| 20 | | 0.557 | | |
| 21 | | 0.569 | | |
| 22 | | 1.581 | 30% at 30 μM | |
| 23 | | 1.588 | | |
| 24 | | 1.944 | | |
| 25 | | 2.363 | | |
| 26 | | 2.609 | 50% at 30 μM | |
| 27 | | 2.269 | | |
| 28 | | 3.670 | | |
| 29 | | 5.331 | | |
| 30 | 105 | | | 10 |
| 31 | | 0.226 | | |
| 32 | | 0.028 | | |
| 33 | | 0.052 | | |
| 34 | | 0.098 | | |
| 35 | | 0.121 | | |
| 36 | | 0.129 | | |
| 37 | | 0.237 | | |
| 38 | | 0.412 | | |
| 39 | | 0.497 | | |
| 40 | | 0.651 | 30% at 30 μM | |
| 41 | | 0.872 | | |
| 42 | | 0.920 | | |
| 43 | | >1.000 | | |
| 44 | | 1.481 | | |
| 45 | | 1.755 | | |
| 46 | | 1.814 | | |
| 47 | | 1.911 | | |
| 48 | | 1.945 | | |
| 49 | | 0.418 | | 3 |
| 50 | | 0.179 | | |
| 51 | | 0.887 | | |
| 52 | | 2.346 | | |

TABLE 1-continued

| Compound of Example No. | In Vitro | | In Vivo (Cell Culture) | |
|---|---|---|---|---|
| | % Inhibition | $IC_{50}$ μM | % Inhibition | $IC_{50}$ μM |
| 53 | | 0.047 | | 0.54 |
| 54 | | 0.158 | | |
| 55 | | 0.114 | | |
| 57 | | 0.399 | | |
| 89 | | 0.186 | | |
| 89 | | 0.614 | | |
| 90 | | 0.604 | | |
| 91 | | 2.071 | | |
| 92 | | 0.253 | | |
| 93 | | 0.521 | | |
| 95 | | 1.001 | | |
| 96 | | 0.374 | | |
| 100 | | 1.994 | | |
| 184 | | 0.278 | | |
| 186 | | 0.555 | | |
| 187 | | 0.561 | | |
| 188 | | 0.771 | | |
| 189 | | 0.859 | | |
| 190 | | 0.921 | | |
| 191 | | 1.355 | | |
| 192 | | 1.797 | | |
| 193 | | 2.902 | | |
| 194 | | 4.952 | | |
| 195 | | 12.831 | | |
| 208 | | 1.215 | | |
| 209 | | 1.372 | | |
| 211 | | >0.1 | | |
| 212 | | 0.034 | | |
| 213 | | 0.062 | | |
| 214 | | 0.303 | | |
| 215 | | 0.031 | | |
| 216 | | 1.000 | | |
| 217 | | >1.00 | | |
| 218 | | 0.051 | | |
| 219 | | 0.108 | | |
| 220 | | 0.029 | | |
| 221 | | 0.002 | | |
| 222 | | 0.085 | | |
| 223 | | 0.043 | | |
| 224 | | 0.028 | | |

The invention compounds will be utilized to treat subjects suffering from cancer and other proliferative diseases, immunodeficiency, and certain degenerative diseases, and in need of treatment. The compounds are ideally suited to treating psoriasis, restenosis, autoimmune disease, and atherosclerosis. The compounds will generally be utilized as a pharmaceutical formulation, in which the compound of Formula I is present in a concentration of about 5% to about 95% by weight. The compounds can be formulated for convenient oral, parenteral, topical, rectal, or like routes of administration. The compound will be formulated with common diluents, excipients, and carriers routinely utilized in medicine, for instance, with polyols such as glycerin, ethylene glycol, sorbitol 70; mono- and difatty acid esters of ethylene glycol. Starches and sugars such as corn starch, sucrose, lactose, and the like, can be utilized for solid preparations. Such solid formulations can be in the form of tablets, troches, pills, capsules, and the like. Flavoring agents such as peppermint, oil of wintergreen, and the like can be incorporated.

Typical doses of active compound are those that are effective to treat the cancer or other proliferative disorder afflicting the mammal. Doses will generally be from about 0.1 mg per kilogram body weight to about 500 mg per kilogram body weight. Such doses will be administered from one to about four times a day, or as needed to effectively treat the cancer, psoriasis, restenosis, or other proliferative disorder.

A preferred method for delivering the invention compound is orally via a tablet, capsule, solution, or syrup. Another method is parenterally, especially via intravenous infusion of a solution of the benzopyran in isotonic saline or 5% aqueous glucose.

Following are typical formulations provided by the invention.

EXAMPLE 225
Preparation of 50-mg Tablets

| Preparation of 50-mg Tablets | | |
|---|---|---|
| Per Tablet | | Per 10,000 Tablets |
| 0.050 g | 4-fluoro-2-(4-iodo-2-methyl-phenylamino)-benzoic acid | 500 g |
| 0.080 g | lactose | 800 g |
| 0.010 g | corn starch (for mix) | 100 g |
| 0.008 g | corn starch (for paste) | 80 g |
| 0.002 g | magnesium stearate (1%) | 20 g |
| 0.150 g | | 1500 g |

The benzoic acid, lactose, and corn starch (for mix) are blended to uniformity. The corn starch (for paste) is suspended in 600 mL of water and heated with stirring to form a paste. The paste is used to granulate the mixed powders. The granules are passed through a #8 screen and dried at 120° F. The dry granules are passed through a #16 screen. The mixture is lubricated with 1% magnesium stearate and compressed into tablets. The tablets are administered to a mammal for inhibiting MEK enzymes and treating restenosis, atherosclerosis, and psoriasis.

EXAMPLE 226
Preparation of Oral Suspension

| Preparation of Oral Suspension | |
|---|---|
| Ingredient | Amount |
| 5-Chloro-2-(4-iodo-2-methyl-phenylamino)-N-(methyl)-benzamide | 500 mg |
| Sorbitol solution (70% NF) | 40 mL |
| Sodium benzoate | 150 mg |
| Saccharin | 10 mg |
| Red dye | 10 mg |
| Cherry flavor | 50 mg |
| Distilled water qs ad | 100 mL |

The sorbitol solution is added to 40 mL of distilled water and the benzamide derivative is suspended therein. The saccharin, sodium benzoate, flavor, and dye are added and dissolved. The volume is adjusted to 100 mL with distilled water. Each milliliter of syrup contains 5 mg of the invention compound. The syrup is administered to a mammal for treating proliferative disease, especially breast cancer and skin cancer.

EXAMPLE 227
Preparation of Parenteral Solution

In a solution of 700 mL of propylene glycol and 200 mL of water for injection is added 20.0 g of 4-fluoro-2-(4-bromo-2-methyl-phenylamino)-benzyl alcohol. The volume of the solution is adjusted to 1000 mL by addition of water for injection. The formulation is heat sterilized, filled into 50-mL ampoules each containing 2.0 mL (40 mg of 4-fluoro-2-(4-bromo-2-methyl-phenylamino)-benzyl), and sealed under nitrogen.

The invention compound thus formulated will be administered to a mammal in need of treatment for a proliferative disorder such as cancer, psoriasis, restenosis, atherosclerosis, autoimmune disease, and other immunodeficient diseases and degenerative disorders, at a rate and dose effective to treat the condition. An "antiproliferative amount" of an invention compound is that quantity of compound that inhibits or reduces the rate of proliferation of target cells. Typical cancers to be treated according to this invention include breast cancer, colon cancer, prostate cancer, skin cancer, and the like. The invention compound is especially well-suited for use in combination with radiation for treating cancer. The compound is well-suited to the treatment of psoriasis, restenosis, and atherosclerosis, and to inhibiting the activity of MEK enzymes, especially $MEK_1$ and $MEK_2$. All that is required to inhibit these enzymes is to administer to a mammal an MEK inhibiting amount of a compound of the invention. An "MEK inhibiting amount" of an invention compound is an amount that when administered to a mammal causes a measurable inhibition of the MEK enzyme. Typical MEK inhibiting amounts will be from about 0.1 μg to about 500 mg of active compound per kilogram body weight. For treating the proliferative diseases mentioned above, typical doses will be from about 0.1 to about 50 mg/kg, normally given from one to about four times per day.

We claim:

1. A compound of the formula:

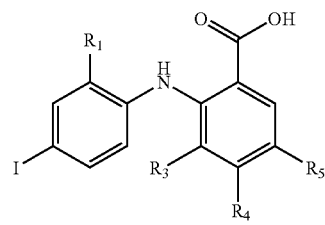

wherein:

$R_1$ is halo or $CH_3$; and $R_3$, $R_4$ and $R_5$ are independently halo or hydrogen; or a pharmeceutically acceptable salt from thereof.

2. A compound of claim 1, wherein the compound is selected from:

4-Fluoro-2-(4-iodo-2-methylphenylamino)benzole acid;

3,4,6-Trifluoro-2-(4-iodo-2-methyl-phenylamino)-benzoic acid;

3,4-Difluoro-2-(4-iodo-2-methyl-phenylamino)-benzoic acid;

5-Bromo-3,4-difluoro-2-(4-iodo-2-methyl-phenylamino)-benzoic acid;

5-Chloro-2-(4-iodo-2-methyl-phenylamino)-benzoic acid;

5-Bromo-2-(4-iodo-2-methyl-phenylamino)-benzoic acid;

4-Chloro-2-(4-iodo-2-methyl-phenylamino)-benzoic acid;

2-(4-Iodo-2-methyl-phenylamino)-benzoic acid;

5-Fluoro-2-(4-iodo-2-methyl-phenylamino)-benzoic acid; or

5-Iodo-2-(4-iodo-2-methyl-phenylamino)-benzoic acid;

or pharmaceutically acceptants that form thereof.

3. A method of treating a mammal suffering from stroke comprising administering to the mammal a pharmaceutically effective amount of a compound of claim 1.

4. A method of treating a mammal suffering from heart failure comprising administering to the mammal a pharmaceutically effective amount of a compound of claim 1.

5. A method of treating a mammal suffering from hepatomegaly comprising administering to the mammal a pharmaceutically effective amount of a compound of claim 1.

6. A method of treating a mammal suffering from cardiomegaly comprising administering to the mammal a pharmaceutically effective amount of a compound of claim 1.

7. A method of treating a mammal suffering from diabetes comprising administering to the mammal a pharmaceutically effective amount of a compound of claim 1.

8. A method of treating a mammal suffering from cancer comprising administering to the mammal a pharmaceutically effective amount of a compound of claim 1, wherein the cancer is breast cancer, prostate cancer, pancreatic cancer, colon cancer or skin cancer.

9. A method of treating a mammal suffering from psoriasis comprising administering to the mammal a pharmaceutically effective amount of a compound of claim 1.

10. A method of treating a mammal suffering from restenosis comprising administering to the mammal a pharmaceutically effective amount of a compound of claim 1.

11. A method of treating a mammal suffering from atheroactarosis comprising administering to the mammal a pharmaceutically effective amount of a compound of claim 1.

* * * * *

UNITED STATES PATENT AND TRADEMARK OFFICE
CERTIFICATE OF CORRECTION

PATENT NO. : 7,019,033 B2
APPLICATION NO. : 10/315654
DATED : March 28, 2006
INVENTOR(S) : Stephen Douglas Barrett et al.

It is certified that error appears in the above-identified patent and that said Letters Patent is hereby corrected as shown below:

Column 24
Line 48, "benzole" should read -- benzoic --

Column 24
Line 49, "2,4,6-Trifluoro" should read -- 3,4,5-Trifluoro --

Column 24
Line 67, "pharmaceutically acceptants that form thereof" should read --pharmaceutically acceptable salt form thereof --

Column 26
Lines 12 to 13, "atheroactarosis" should read -- atherosclerosis --

Signed and Sealed this

Thirteenth Day of February, 2007

JON W. DUDAS
*Director of the United States Patent and Trademark Office*